(12) United States Patent
Dibari et al.

(10) Patent No.: US 11,581,093 B2
(45) Date of Patent: Feb. 14, 2023

(54) AUTOMATIC DETECTION OF MENTAL HEALTH CONDITION AND PATIENT CLASSIFICATION USING MACHINE LEARNING

(71) Applicant: International Business Machines Corporation, Armonk, NY (US)

(72) Inventors: Maria Dibari, Hopewell Junction, NY (US); Alonso Diaz, Morgan Hill, CA (US)

(73) Assignee: MERATIVE US L.P., Ann Arbor, MI (US)

( * ) Notice: Subject to any disclaimer, the term of this patent is extended or adjusted under 35 U.S.C. 154(b) by 306 days.

(21) Appl. No.: 16/576,199

(22) Filed: Sep. 19, 2019

(65) Prior Publication Data

US 2021/0090733 A1 Mar. 25, 2021

(51) Int. Cl.
*G16H 50/20* (2018.01)
*A61B 5/16* (2006.01)
(Continued)

(52) U.S. Cl.
CPC ............. *G16H 50/20* (2018.01); *A61B 5/165* (2013.01); *G06F 40/20* (2020.01); *G16H 10/40* (2018.01);
(Continued)

(58) Field of Classification Search
CPC ........ G16H 50/20; G16H 10/40; G16H 10/60; G16H 50/30; G06F 40/20; G06N 20/00; A61B 5/165
(Continued)

(56) References Cited

U.S. PATENT DOCUMENTS

| 6,694,298 B1 | 2/2004 | Teagarden et al. |
| 7,693,727 B2 | 4/2010 | Moore |

(Continued)

FOREIGN PATENT DOCUMENTS

WO 2018/223172 A1 12/2018

OTHER PUBLICATIONS

J.R. Cutcliffe, et al., "The Nurses' Global Assessment of Suicide Risk (NGASR): developing a tool for clinical practice", Journal of Psychiatric and Mental Health Nursing, 2004, 11, 393-400, 8 pages.

(Continued)

*Primary Examiner* — John A Pauls
(74) *Attorney, Agent, or Firm* — Edell, Shapiro & Finnan, LLC (57) ABSTRACT

Methods and systems are provided for detecting a mental health condition. Structured and unstructured information is analyzed using natural language processing to extract information including clinical data values and medical concepts pertaining to a user. Reference medical information is evaluated using natural language processing to correlate medical data with mental health conditions. A classification for a mental health condition of the user is determined using a machine learning model and based on the extracted information and correlations, wherein the extracted information includes blood analysis for the user. The user is assigned to a segment of users based on the extracted information. A treatment for the mental health condition of the user is indicated based on the classification and the assigned segment of users.

20 Claims, 7 Drawing Sheets

(51) Int. Cl.
*G16H 10/60* (2018.01)
*G16H 50/30* (2018.01)
*G16H 10/40* (2018.01)
*G06F 40/20* (2020.01)
*G06N 20/00* (2019.01)

(52) U.S. Cl.
CPC ............. *G16H 10/60* (2018.01); *G16H 50/30* (2018.01); *G06N 20/00* (2019.01)

(58) Field of Classification Search
USPC ......................................................... 705/2–3
See application file for complete search history.

(56) References Cited

U.S. PATENT DOCUMENTS

| | | | |
|---|---|---|---|
| 10,068,060 | B2 | 9/2018 | Madan et al. |
| 10,204,707 | B2 | 2/2019 | Pestian et al. |
| 10,276,190 | B2 | 4/2019 | Ashoori et al. |
| 10,319,477 | B1* | 6/2019 | Bill ........................ G16H 50/30 |
| 10,629,303 | B2* | 4/2020 | Schulte .................. G16H 50/20 |
| 2003/0135128 | A1* | 7/2003 | Suffin ..................... A61B 5/411 600/544 |
| 2013/0297536 | A1 | 11/2013 | Mmosni et al. |
| 2014/0052475 | A1 | 2/2014 | Madan et al. |
| 2014/0095204 | A1* | 4/2014 | Fung ...................... G16H 50/20 705/3 |
| 2014/0257708 | A1* | 9/2014 | Bilello ................... G16B 20/00 702/19 |
| 2015/0193583 | A1* | 7/2015 | McNair .................. G16H 50/20 705/2 |
| 2015/0370994 | A1* | 12/2015 | Madan ................... G16H 50/50 705/3 |
| 2016/0188597 | A1* | 6/2016 | Moore .............. G06F 16/24578 707/749 |
| 2019/0079916 | A1 | 3/2019 | Eyigoz |
| 2019/0313903 | A1* | 10/2019 | McKinnon ........... A61B 3/0025 |

OTHER PUBLICATIONS

R. Jackson, et al., "Natural language processing to extract symptoms of severe mental illness from clinical text: the Clinical Record Interactive Search Comprehensive Data Extraction (CRIS-CODE) project", BMJ Open 2017;6:e012012. doi:10.1136/bmjopen-2016-012012, Jan. 17, 2017, 10 pages.

D. Joshi, et al., "Mental health analysis using deep learning for feature extraction", CoDS-COMAD '18, Jan. 11-13, 2018, Goa, India, 2018 Association for Computing Machinery, ACM ISBN 978-1-4503-6341, 4 pages.

N. Carson, et al., "Identification of suicidal behavior among psychiatrically hospitalized adolescents using natural language processing and machine learning of electronic health records", Research Article, PLOS One (https://doi.org/10.1371/journal.pone.0211116), Feb. 19, 2019, 14 pages.

G. Gkotsis, et al., "Characterisation of mental health conditions in social media using Informed Deep Learning", Scientific Reports, 7:45141, Mar. 22, 2017, 11 pages.

R. Calvo, et al., "Natural language processing in mental health applications using non-clinical texts", Natural Language Engineering, vol. 23, Issue 5, Jan. 2017, 37 pages.

B. Cook, et al., "Novel Use of Natural Language Processing (NLP) to Predict Suicidal Ideation and Psychiatric Symptoms in a Text-Based Mental Health Intervention in Madrid", Research Article, Computational and Mathematical Methods in Medicine, vol. 2016, Article ID 8708434, 2016, 8 pages.

* cited by examiner

AUTOMATIC DETECTION OF MENTAL HEALTH CONDITION AND PATIENT CLASSIFICATION USING MACHINE LEARNING

BACKGROUND

1. Technical Field

Present invention embodiments relate to machine learning systems to detect mental health risk, and in particular, to automate detection of and classification of a patient as having a particular mental health condition.

2. Discussion of the Related Art

Mental disorders and diseases impact a significant portion of the population. Yet, these disorders and diseases are often difficult to diagnose and treat. According to the National Institute of Mental Health, approximately one in five Americans will experience a mental disorder in a given year, with one in twenty five adults experiencing a serious mental disorder that may substantially interfere with or limit one or more major life activities.

Lifetime risks for mental disorders and diseases may be higher. According to the Centers for Disease Control and Prevention, more than half of the population will be diagnosed with a mental illness or disorder at some point in their lifetime. Serious mental disorders may include but are not limited to schizophrenia, bipolar disorder, anxiety, or major depression. Depression is reportedly the third most common cause of hospitalization in the United States for those in the 18-44 age range.

Primary care physicians report not being equipped to diagnose or manage mental health disorders and diseases. Accordingly, only a fraction of patients with mental health disorders receive appropriate diagnoses and services when evaluated by their primary health care provider. Additionally, primary care physicians and other medical services report difficulty in coordinating and communicating with other mental health providers, which contributes to lack of preparedness and inability to support patients at risk of or having a mental health condition.

SUMMARY

According to embodiments of the present invention, methods, systems, and computer readable media are provided for detecting a mental health condition. Structured and unstructured information is analyzed using natural language processing to extract information including clinical data values and medical concepts pertaining to a user. Reference medical information is evaluated using natural language processing to correlate medical data with mental health conditions. A classification for a mental health condition of the user is determined using a machine learning model and based on the extracted information and correlations, wherein the extracted information includes blood analysis for the user. The user is assigned to a segment of users based on the extracted information. A treatment for the mental health condition of the user is indicated based on the classification and the assigned segment of users.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

DETAILED DESCRIPTION

Methods, systems, and computer readable media are provided for detection and monitoring of mental health conditions. Structured and unstructured information is analyzed using natural language processing to extract information including clinical data values and medical concepts pertaining to a user. Reference medical information is evaluated using natural language processing to correlate medical data with mental health conditions. A classification for a mental health condition of the user is determined using a machine learning model (e.g., using natural language processing) and based on the extracted information and correlations, wherein the extracted information includes blood analysis for the user. The user is assigned to a segment of users based on the extracted information. A treatment for the mental health condition of the user is indicated based on the classification and the assigned segment of users. The patient may continue to be monitored by the system, after diagnosis, to determine whether the mental health condition of the patient is improving.

Figure 1:
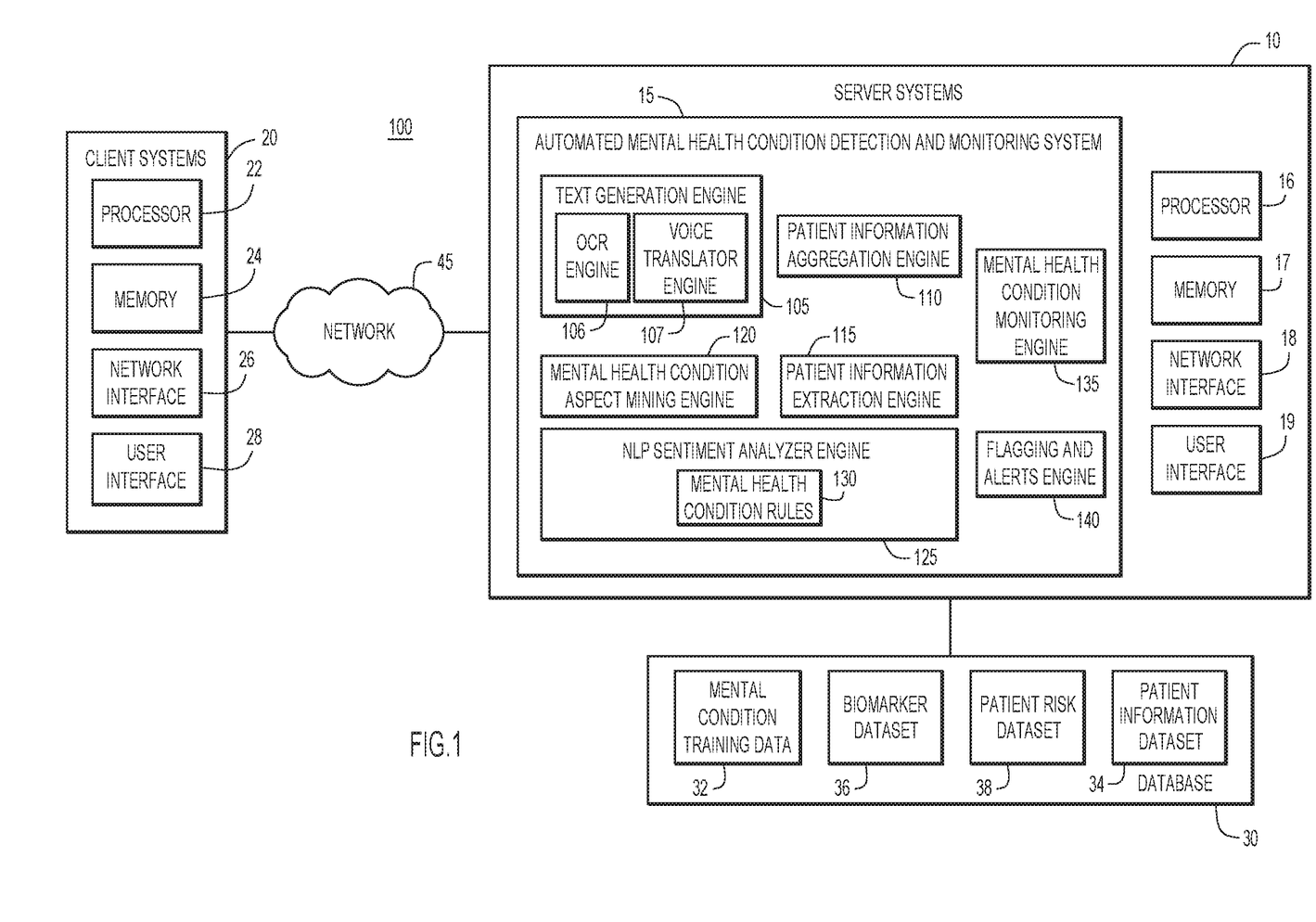
FIG. 1 is a diagrammatic illustration of an example computing environment for detecting a mental health condition according to an embodiment of the present invention.

An example environment for use with present invention embodiments is illustrated in FIG. 1. Specifically, the environment includes one or more server systems 10, one or more client or end-user systems 20, a database 30, and network 45. Server systems 10 and client systems 20 may be remote from each other and may communicate over a network 45. The network may be implemented by any number of any suitable communications media, such as a wide area network (WAN), a local area network (LAN), Internet, Intranet, etc. Alternatively, server systems 10 and client systems 20 may be local to each other, and may communicate via any appropriate local communication medium, such as local area network (LAN), hardwire, wireless link, Intranet, etc.

Client systems 20 enable users to submit datasets to server systems 10 for training an automated mental health condition detection and monitoring system 15 and for using this system to monitor ongoing status of at-risk patients. The server systems 10 include an automated mental health condition detection and monitoring system 15 comprising a text generation engine 105, a patient information aggregation engine 110, a patient information extraction engine 115, a mental health condition aspect mining engine 120, a NLP sentiment analyzer engine 125, a mental health condition monitoring engine 135, and flagging and alerts engine 140, as described herein.

A database 30 may store various information for the analysis, such as mental condition training data 32, biomarker dataset 36, patient information dataset 34, and patient risk dataset 38, etc. The mental condition training data 32 contains files with labeled information to train a system 15 comprising a NLP classifier to identify a likelihood of having a mental condition. Once trained, the system 15 may be used to identify patients who are at risk of or who have characteristics of a particular mental condition. In some aspects, the mental condition training dataset may comprise a dataset for each mental condition. For example, an annotated dataset may be provided corresponding to patients diagnosed with major depression, another annotated dataset may be provided corresponding to patients diagnosed with anxiety, etc. This allows the system to be trained to identify specific mental conditions.

Biomarker dataset 36 corresponds to known biomarkers that are associated with specific mental health conditions. Biomarkers may be derived from genomic, proteomic, and/or immunoassay studies. The biomarker dataset 36 may be incorporated into training data for mental health condition detection and monitoring system 15 to identify patients at risk or having a mental condition associated with specific biomarkers.

Patient information dataset 34 corresponds to information pertaining to a specific patient, including medical files, imaging studies, physician notes, blood analysis results, information stored in electronic health records for a specific patient as well as voice data pertaining to voicemails, teleconferences, recorded calls from assistance programs that are translated into text for analysis.

Patient risk dataset 38 includes information pertaining to patients who are determined to be at risk and/or are being monitored by the system. This information may include one or more conditions for which the patient is at risk of or likely to have, as well as sentiment changes over a time period. In some aspects, the patient risk dataset 38 may be analyzed to determine whether therapy and/or other treatments are improving the mental condition of a patient over time.

The database system 30 may be implemented by any conventional or other database or storage unit, may be local to or remote from server systems 10 and client systems 20 and may communicate via any appropriate communication medium, such as local area network (LAN), wide area network (WAN), Internet, hardwire, wireless link, Intranet, etc. The client systems may present a graphical user interface, such as a GUI, etc., or other interface, such as command line prompts, menu screens, etc., to solicit information from users pertaining to the desired datasets, patient health information, and may provide reports including analysis results of the patient information dataset, including patients at risk for a specific mental condition and a sentiment score as ascertained by the system.

Server systems 10 and client systems 20 may be implemented by any conventional or other computer systems preferably equipped with a display or monitor, a base (including at least one hardware processor (e.g., microprocessor, controller, central processing unit (CPU), etc.), one or more memories and/or internal or external network interfaces or communications devices (e.g., modem, network cards, etc.), optional input devices (e.g., a keyboard, mouse or other input device), and any commercially available and custom software (e.g., server/communications software, automated mental health condition detection and monitoring system software, browser/interface software, etc.). By way of example, the server/client includes at least one processor 16, 22 one or more memories 17, 24 and/or internal or external network interfaces or communications devices 18, 26 such as a modem or network cards, and a user interface 19, 28 etc. The optional input devices may include a keyboard, mouse, or other input device.

Alternatively, one or more client systems 20 may perform automated mental health condition detection and monitoring as a stand-alone unit. In a stand-alone mode of operation, the client system stores or has access to the data, such as mental condition training data 32, patient information dataset 34, biomarker dataset 36 and may generate patient risk dataset 38. The stand-alone unit includes automated mental health condition detection and monitoring system 15. The graphical user or other interface 19, 28, such as a GUI, command line prompts, menu screens, etc., solicits information from a corresponding user pertaining to the desired patient data, and may provide reports including analysis results of a level of risk for a patient for one or more mental health conditions.

Automated mental health condition detection and monitoring system 15 may include one or more modules or units to perform the various functions of present invention embodiments described herein. The various modules, text generation engine 105, patient information aggregation engine 110, patient information extraction engine 115, mental health condition aspect mining engine 120, NLP sentiment analyzer engine 125, mental health condition monitoring engine 135, and flagging and alerts engine 140, etc., may be implemented by any combination of any quantity of software and/or hardware modules or units, and may reside within memory 17 of the server for execution by processor 16. These modules are described in additional detail below.

Text generation engine 105 may be configured to generate text from non-text sources. Text generation engine 105 may comprise an optical character recognition engine 106 that converts non-readable text to machine readable text. In other aspects, text generation engine may comprise a voice translation engine 107 that generates machine readable text from a voice recording or from live speech. The machine readable text may be stored in database 30, as part of patient information dataset 34, for further analysis.

Patient information aggregation engine 110 may aggregate information originating from different sources for a particular patient. This information may include biomarkers, EMR information, employee assistance transcriptions, physician notes and other sources for a patient. In some aspects, this engine may generate a unique identifier for the patient with which to associate incoming patient information.

Patient information extraction engine 115 may comprise a natural language processor to identify relevant phrases pertaining to mental health conditions from machine readable text stored in the patient information dataset. Examples of relevant phrases include terms to describe how the patient is feeling (e.g., overwhelmed, anxious, sad, content, happy, ecstatic, etc.), terms to describe urgency of an action (e.g., immediately, urgently, etc.), terms specific to particular mental health conditions, biomarkers, etc. In other aspects, this engine may analyze extracted text for phrases that are associated with mental disorders. For example, depression may be associated with a specific set of phrases, while bipolar disorder may be associated with other sets of phrases, etc. These phrases may be established based on a Diagnostic and Statistical Manual of Mental Disorders (DSM) classification system, which lists mental disorder standards.

Once this information is extracted, NLP Sentiment Analyzer Engine 125 may perform analysis on the extracted text to determine sentiment. For example, words, phrases, or groups of words may be associated with a positive sentiment, while other words, phrases or groups of words may be associated with a negative sentiment. In other cases, words or phrases may be considered to be neutral. NLP sentiment analyzer engine may determine sentiment as a function of time, e.g., by analyzing extracted text associated with a specified time frame together. The output may be represented as a sentiment trajectory, e.g., which shows a change in sentiment as a function of days, weeks, months, or more.

Mental health condition rules 130 may provide numerical values for scoring various words, phrases and other information for determination of sentiment analysis. For example, words, phrases and groups of words may be associated with a subcategory of positive sentiments (e.g., positive, highly positive), or associated with a subcategory of negative sentiments (e.g., negative, highly negative), with words in each category associated with a score. Similarly, biomarker data may be associated with a value that is incorporated into sentiment determination. For example, specific biomarkers may be associated with specific values that are summed with words and/or phrases scored based on positive or negative sentiment.

For example, a patient may be determined to be at-risk if the patient has specific biomarkers associated with depression and the sentiment analyzer determines sentiment as being negative, e.g., for a given period of time, and/or associated with depression. The system may aggregate (e.g., by summing or performing weighted summing, etc.), individually scored words, phrases, or groups of words and combine with biomarker values to reach an aggregate score. If the aggregate score exceeds a threshold value, the user may be determined to be at-risk for or to have depression.

Mental health condition monitoring engine 135 may perform ongoing monitoring of patients with an aggregate score over a threshold value, e.g., determined to have a condition or have a high risk of the condition. For example, a patient at high risk may be monitored to determine changes in sentiment (e.g., whether sentiment becomes increasingly negative). Alternatively, a patient diagnosed with and receiving treatment for a condition may be monitored to determine whether sentiment is improving.

Flagging and alerts engine 140 may send out notification to physicians or other health care professionals, when a change in sentiment exceeds a threshold, to ensure timely intervention.

Figure 2:
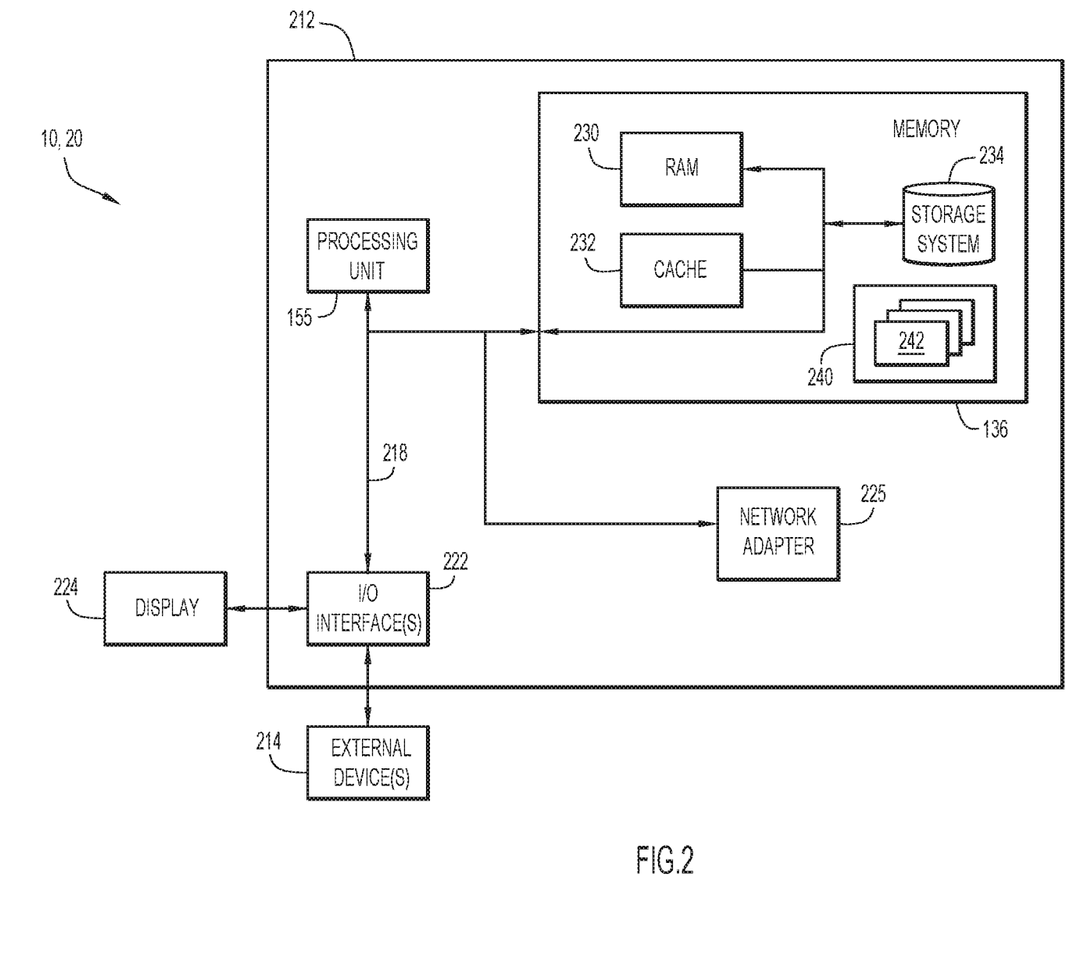
FIG. 2 is an example computing device for the computing environment of FIG. 1, according to an embodiment of the present invention.

Client systems 20 and server systems 10 may be implemented by any suitable computing device, such as computing device 212 shown in FIG. 2 for computing environment 100. This example is not intended to suggest any limitation as to the scope of use or functionality of embodiments of the invention described herein. Regardless, computing device 212 is capable of being implemented and/or performing any of the functionality set forth herein.

In the computing device, there is a computer system which is operational with numerous other general purpose or special purpose computing system environments or configurations. Examples of well-known computing systems, environments, and/or configurations that may be suitable for use with the computer system include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules (e.g., automated mental health condition detection and monitoring system 15 and its corresponding modules), being executed by a computer system. Generally, program modules may include routines, programs, objects, components, logic, data structures, and so on that perform particular tasks or implement particular abstract data types.

Computer system 212 is shown in the form of a general-purpose computing device. The components of computer system 212 may include, but are not limited to, one or more processors or processing units 155, a system memory 136, and a bus 218 that couples various system components including system memory 136 to processor 155.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and it includes both volatile and non-volatile media, removable and non-removable media.

System memory 136 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 136 may include at least one program product having a set (e.g., at least one) of program modules that are configured to carry out the functions of embodiments of the invention.

Program/utility 240, having a set (at least one) of program modules 242 (e.g., automated mental health condition detection and monitoring system 15 and corresponding modules, etc.) may be stored in memory 136 by way of example, and not limitation, as well as an operating system, one or more application programs, other program modules, and program data. Each of the operating system, one or more application programs, other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 225. As depicted, network adapter 225 communicates with the other components of computer system 212 via bus 218. It should be understood that although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
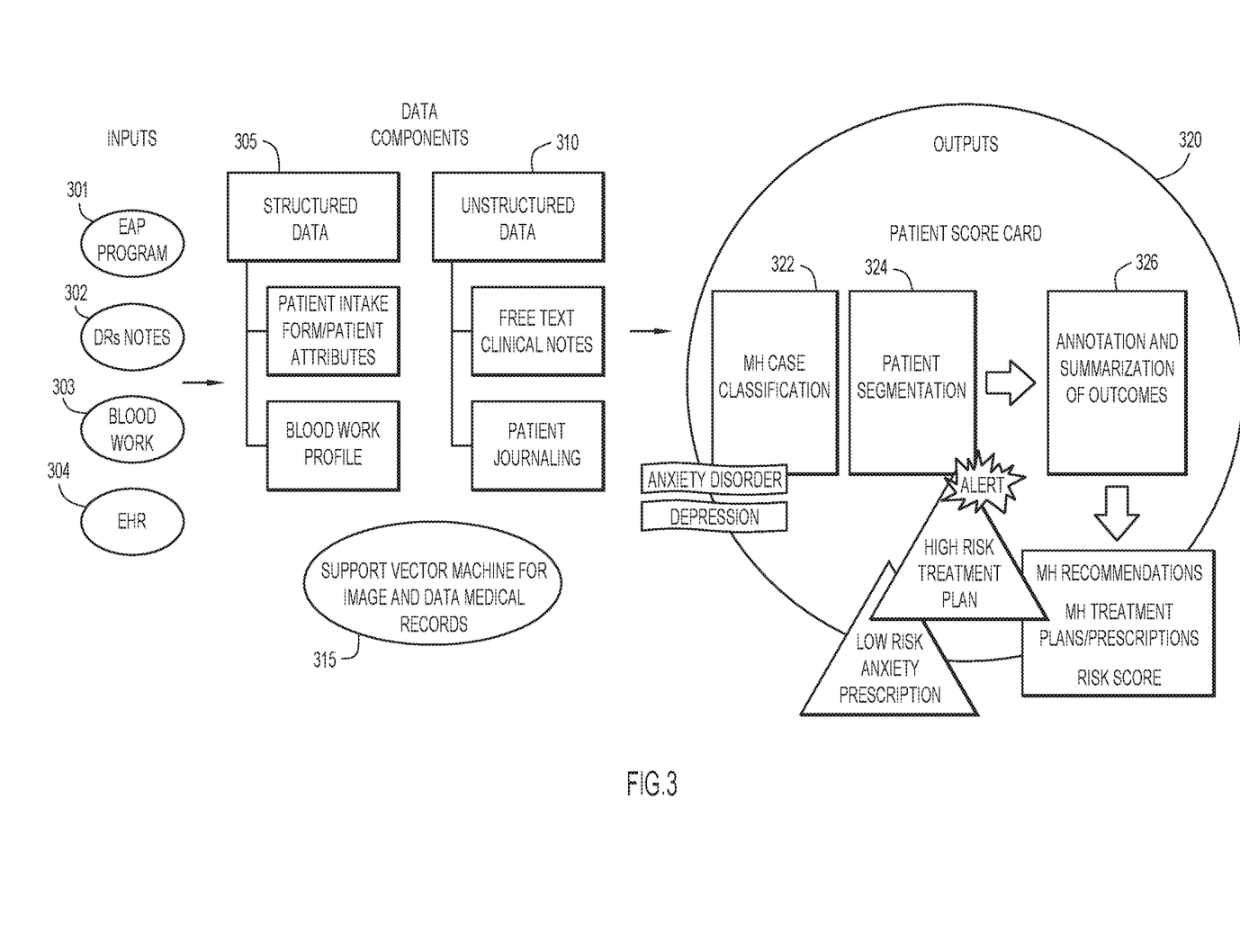
FIG. 3 is a diagram illustration showing example data components of an automated mental health condition detection system, according to an embodiment of the present invention.

FIG. 3 shows components of the mental health detection and monitoring system. Inputs may include employee assistance program (EAP) recordings 301, physician notes 302, biomarkers 303, and electronic health records (EHR) 304. Inputs may be stored as structured data 305 (e.g., blood work profiles, physician notes, patient case files, electronic health records, and patient attributes) or as unstructured data 310 (e.g., free text, patient journaling, text transcripts, notes of a clinician, a patient journal, medical literature, and medical standards, or other machine readable text, etc.). The structured and unstructured text may be analyzed by a machine learning based system including patient information extraction engine 115. A trained extraction engine may extract medical information from a corpus of data using continuous NPL scanning and analysis of information. In some aspects, the machine learning system comprises a support vector machine 315, which may perform classification based on a separating hyperplane, when trained with labeled training data.

In some aspects, the output of the system may be a patient score card 320 comprising multiple components. The score card may contain a mental health case classification 322, which may include one or more mental health conditions that a patient is at-risk of developing or may already have (e.g., anxiety, depression, etc.). The score card may include patient segmentation 324, which may include a listing of patients subdivided according to risk level, and includes appropriate treatment plans (including one or more additional blood tests to perform based on the classification) for that risk level. The score card may also contain annotation and summarization of outcomes 326, which includes mental health recommendations and mental health treatment plans or prescriptions plans based on a patient's risk score. In other aspects, the score card may list a probable diagnosis with a risk indication (e.g., a probability, a low, medium or high risk category, etc.). The patient may be concurrently scored for two or more mental health conditions, with a score for each condition.

Figure 4:
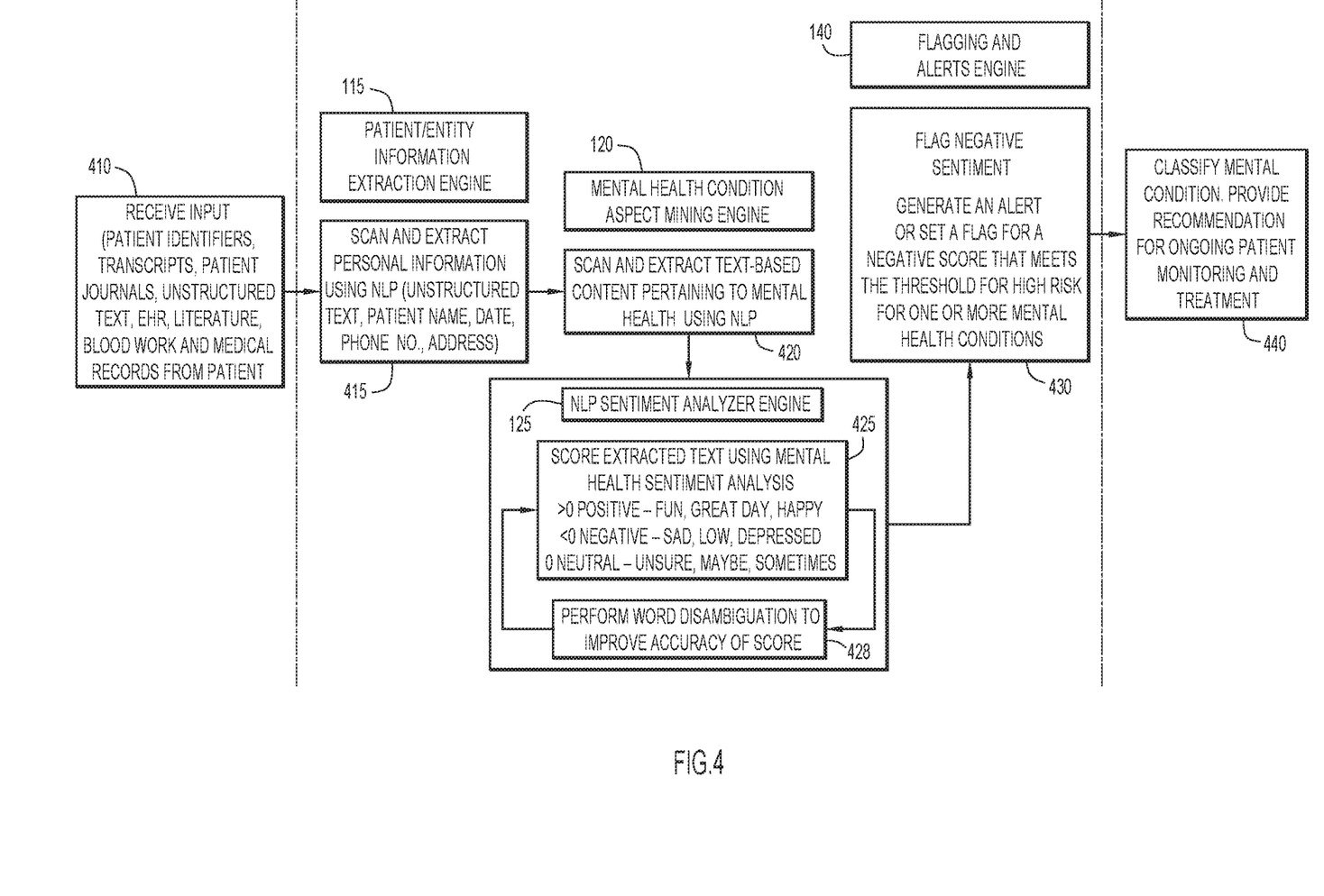
FIG. 4 is a flow diagram of example operations for an automated mental health condition detection system, according to an embodiment of the present invention.

FIG. 4 shows data flow through the mental health condition detection and monitoring system 15. At operation 410, inputs are received by the system. This includes patient identifiers, transcripts of phone calls, physician or patient journal entries, electronic health records, medical literature, information containing biomarkers, or other structured or unstructured forms of text.

At operation 415, the system performs patient and entity recognition using patient information extraction engine 115 by scanning and extracting using NLP relevant information, including patient information, patient name, date, phone number, address, blood work, or any other information used to identify the patient. A named entity recognition NLP technique may be used to extract entities in text such as patient name, phone number, date of birth, and location directly from a call or journal entry.

In some aspects, as the patient provides input, such as through patient journaling using an electronic health record or a counseling service (translated into text), the input is scanned and text-based content pertaining to mental health conditions is automatically identified and extracted using machine learning techniques such as NLP. The system 15 may be set up to determine sentiment, based on meaning of a word, phrase, or paragraph, for structured and unstructured data.

As soon as the call recording begins, text translation may begin. Thus, these techniques may occur instantaneously or almost instantaneously as soon as information is recorded. Libraries and dictionaries may be configured to understand the context of discussion between the patient and health personnel. For example, libraries may be constructed to analyze input from the patient, wherein the libraries include terms related to specific mental health disorders (e.g., datasets for a specific mental health condition). In some aspects, a library or dictionary may be generated for each mental health condition being evaluated by the system. For example, the system may connect to online/global dictionaries established by the medical community as standard of case references for diagnosis and treatment of mental disorders. Patients may be triaged, allowing patients considered to have a condition or risk indicative of an emergency to be identified, and for a notification to be generated and sent to a physician immediately for high risk patients.

At operation 420, mental health condition aspect mining engine 120 scans and extracts text-based content pertaining to mental health conditions. This content may include information including clinical data values (e.g., biomarkers) and medical concepts (e.g., relevant terminology of mental disorders) pertaining to a user. In some aspects, natural language processing may be used to perform identification and extraction of terms, based on dictionaries generated from terminology found in DSM standard of care references. In some aspects, the aspect mining engine uses NLP to correlate medical data with mental health conditions, wherein the NLP (e.g., comprising a Naïve Bayes classifier) is trained on reference medical information.

At operation 425, NPL sentiment analyzer engine 125 may generate a sentiment analysis score based upon extracted text. For example, words associated with positive sentiment may be associated with a positive value, while words associated with negative sentiment may be associated with a negative value. Other words that are not positive or negative may be associated with a neutral value. In some cases, any word associated with a positive sentiment may be associated with a fixed positive value (e.g., "+1"). In other cases, words associated with a positive sentiment may be divided into different categories, each category associated with a specific positive value (e.g., "+1," "+3," etc.). This approach allows words with strong positive sentiment (e.g., ecstatic, thrilled, exuberant, etc.) to be distinguished from words with low positive sentiment (e.g., content, satisfied, etc.). Thus, by aspect mining and sentiment analysis, text is processed and key mental health condition terms are extracted and given an aggregate mental health sentiment score, based on a timeframe, amount of text, etc. In some aspects, a Naïve Bayes classifier algorithm may be used to score text and calculate the probability of aggregate data being an emergency vs a non-emergency.

In some aspects, the sentiment score reflects an aggregate score, in which each word is scored for a positive, neutral or negative value, and the individual values are summed to form an aggregate score for the content being considered. In some aspects, the content may be restricted to a particular time frame, allowing a moving average sentiment to be generated. For example, a sentiment score may be generated to cover a period of a week, a month, a quarter, half a year, or more. In some aspects, this information can be used to monitor patient progress.

Based on the aggregate score, a classification for a mental health condition of the user can be determined. The aggregate score is based on extracted information, identified by the machine learning system, and correlation between the extracted information and reference medical information, wherein the extracted information includes blood analysis for the user. The user is assigned to a segment of users (e.g., having a similar risk profile) based on the extracted information.

At operation 428, word disambiguation may be performed to refine the aggregate sentiment score. A word may have a meaning or sentiment that depends on the context of the word. For example, the word "blue" may have multiple meanings that are context-specific, including reference to a color or reference to a sentiment (how a person is feeling). The system may consider the context of the term, and may adjust the sentiment score to reflect the revised meaning of the term. For example, a negative value may be attributed to the word "blue" during sentiment scoring. However, when the word is evaluated in its context ("the sky was blue today"), the context of the word may change to neutral. A similar analysis may be performed for words with positive sentiment. Thus, word disambiguation analysis may refine the sentiment score, if words are erroneously associated with a particular sentiment (e.g., changing from a positive sentiment to a neutral or negative sentiment, changing from a neutral sentiment to a positive or negative sentiment, or changing from a positive sentiment to a neutral or negative sentiment).

At operation 430, flagging and alerts engine 140 may generate alerts and/or set system flags based on identification of negative mental health sentiment. A flag may be set for a negative score that meets the threshold for high risk for one or more mental disorders, and an alert may be generated and transmitted to a physician. At operation 440, the system generates an output to classify the mental condition as well as provide recommendations or ongoing patient monitoring based on the assigned segment.

In some aspects, the system may become customized or tailored to respective patients, as the system receives additional information relating to the respective patient that is validated by medical professionals.

An example of a phone call or patient journal is provided as follows. Phrases associated with sentiment are enclosed in brackets.

"I feel like I [cannot control] my feelings, I [worry] about what people will think. I am [unsure] as to whether I need to see a physician. I am [not a severe case], but I [need help now]. I just [feel tired and unproductive]. I have [felt like this for more than 5 weeks] since my last visit to the doctor."

These phrases may be individually scored and aggregated to generate an overall sentiment for the passage.

Figure 5:
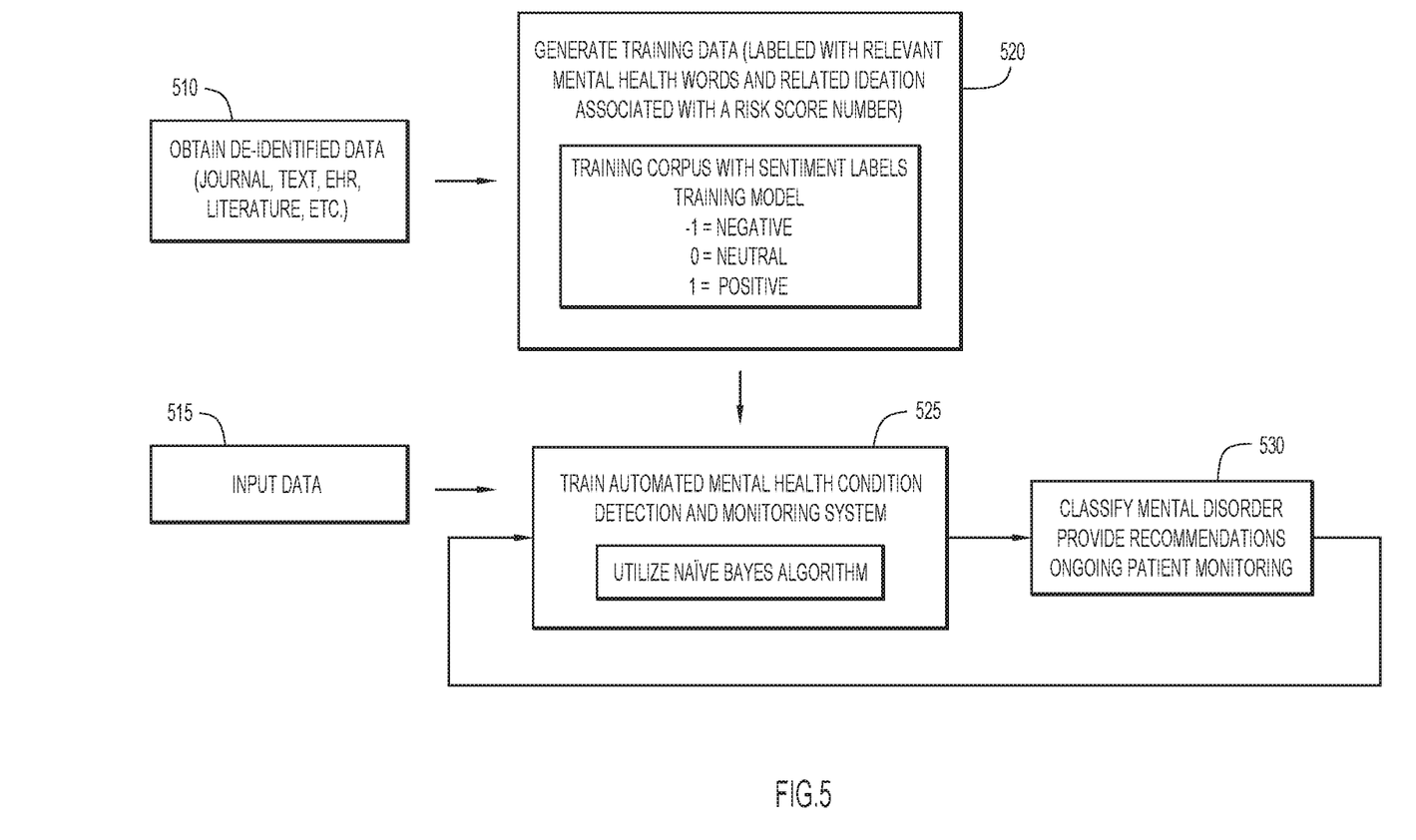
FIG. 5 is a flow diagram of example operations for training an automated mental health condition detection and monitoring system, according to an embodiment of the present invention.

At FIG. 5, example operations are provided for training the mental health condition detection and monitoring system. Training the system may be based on data from actual patient cases, existing EHRs, and screened assistance hotlines that have been labeled with relevant mental health terminology according to standard medical practice. At operation 510, various forms of input data (e.g., patient journals, electronic health records, new studies, new biomarkers, new diagnostic criteria, etc.) may be obtained.

The data may be annotated, at operation 520, to generate training data. For example, words, phrases, and paragraphs may be annotated with relevant mental health terminology, and assigned a related value to generate a risk score. For example, a training model may assign values for sentiment as follows: Negative="−1"; Neutral="0"; Positive="1". Once the corpus of training data has been annotated and scored, the system may be trained on this data at operation 525.

At operation 525, the system is trained on training data, e.g., using a Naïve Bayes Algorithm to calculate the probability of each data instance of being in a given class or category (e.g., Emergency or Non-Emergency). This algorithm may be configured based on entities that it is programmed to identify and customized rules to determine a likeliness of having a mental health condition based on a score. Scores can cause specified outputs (e.g., notification, recommendation, etc.) to be generated and transmitted.

Once the system has been trained using the training data, at operation 515, input data is provided to the system for analysis. The output of the system is reviewed, at operation 530, and the output is validated or invalidated by medical personnel. Medical recommendations may also be reviewed for accuracy.

As previously indicated, training may be performed in a supervised manner, with labeled data. For example, data may be provided to the system (e.g., de-identified patient data), and the system may determine a probable diagnosis, which is later confirmed by a physician. When the classifier is sufficiently trained, correctly identifying patients that are at-risk or that have a mental health condition, the system may be used to identify patients in an unsupervised manner for which a diagnosis is not yet known.

In some aspects, the trained system continues to learn as patient data is analyzed and as diagnoses and predictions are generated and confirmed by the physician.

In some aspects, the training data may be generated based on medical literature (e.g., terms associated with specific mental disorders), mental health standards DSM-5, and/or knowledge of normal versus abnormal biomarkers or other biologic factors.

Figure 6:
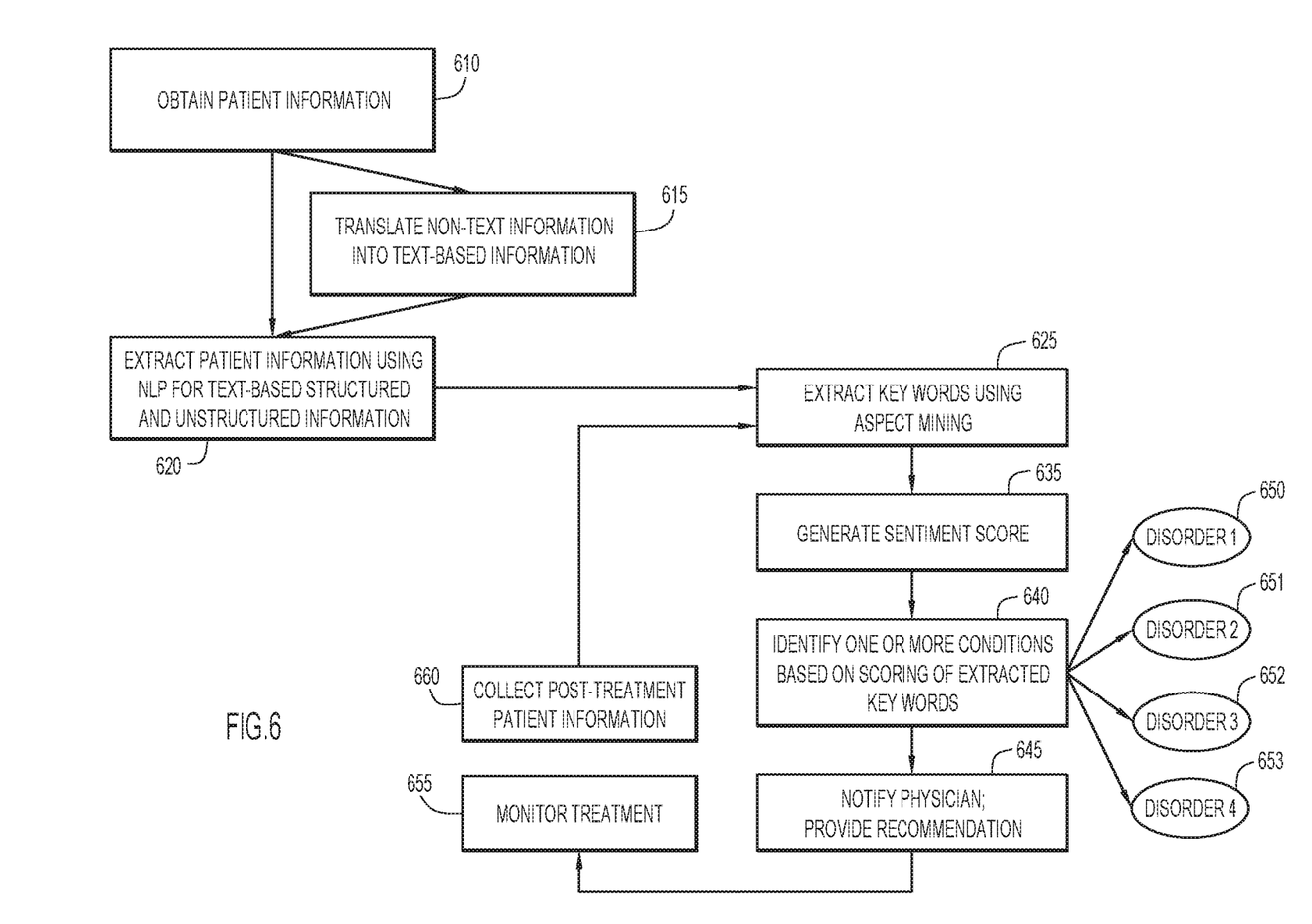
FIG. 6 is a detailed flowchart showing example operations for monitoring patient progress using an automated mental health condition detection system, according to an embodiment of the present invention.

FIG. 6 shows a flowchart including ongoing monitoring aspects of a patient according to the techniques provided herein. At operation 610, patient information is obtained. At operation 615, non-text information is translated into text-based information. Non-text information may include audio recordings of employee assistance calls, emergency hotline calls, or other electronic voice recordings. The system may use a voice to text translator to perform the translation of voice to unstructured text. At operation 620, patient information is extracted using NLP. NLP may be applied to both text-based structured and unstructured information. In some cases, patient information may be extracted from metadata associated with the information. In some aspects, structured information may include information obtained in a database, while unstructured information may include free text or other forms that are not in a database format. At operation 625, keywords related to mental health conditions are extracted from patient input information. At operation 635, sentiment scoring techniques may be applied to the extracted text to generate an aggregate sentiment score. At operation 640, one or more conditions based on the scoring may be identified. For example, the system may identify one or more conditions including any condition (e.g., example conditions 650-653) documented in DSM references. At operation 645, the system may generate a notification that a patient is high risk. The system may provide recommendations/notifications to a physician for monitoring and/or treatment of the patient.

At operation 655, treatment of the patient is monitored. At operation 660, post treatment information may be collected about the patient in order to continue to monitor the progress of the patient. In some aspects, the system may continuously monitoring patient journals within electronic health records to extract and score relevant health information.

For example, if an at-risk patient or patient with a diagnosis begins a treatment program or a new medication, the sentiment of the patient may be monitored over a period of time to determine if the sentiment of the patient is becoming more positive. Additional journaling or EHR information may be analyzed to track the patient. This new information may be analyzed according to operations 630 through 645 as discussed.

Figure 7:
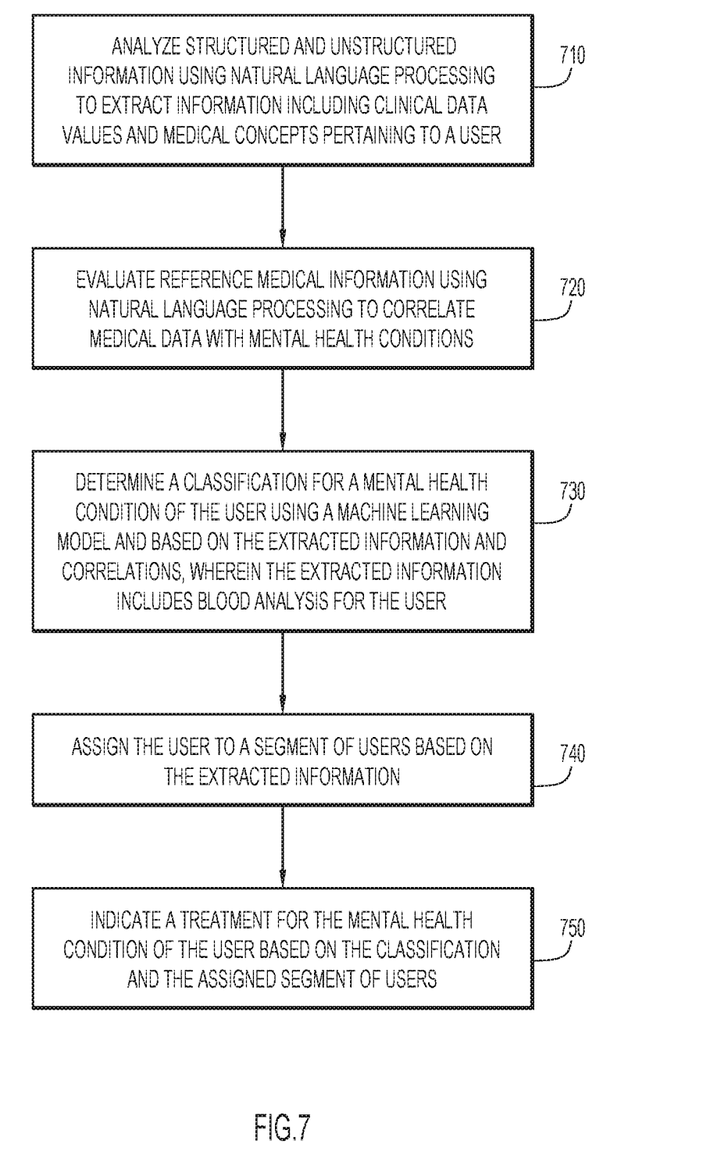
FIG. 7 is a high level flowchart of example operations for mental health condition detection, according to an embodiment of the present invention.

FIG. 7 shows a high level flow diagram of example operations according to the embodiments provided herein. At operation 710, structured and unstructured information is analyzed using natural language processing to extract information including clinical data values and medical concepts pertaining to a user. At operation 720, reference medical information using natural language processing is evaluated to correlate medical data with mental health conditions. At operation 730, a classification for a mental health condition of the user using a machine learning model and based on the extracted information and correlations is determined, wherein the extracted information includes blood analysis for the user. At operation 740, the user is assigned to a segment of users based on the extracted information. At operation 750, a treatment for the mental health condition of the user is indicated based on the classification and the assigned segment of users.

Present techniques provide real-time or near real-time monitoring and identification of at-risk patients in an automated manner, using NLP and machine learning techniques. In some aspects, calls from a patient to an emergency assistance center may be translated and analyzed in real-time or near real-time, allowing at-risk patients to be identified and prompt assistance provided. For example, in urgent cases, alerts or notifications may be provided to 911 services or other emergency personnel, so that patients at high-risk receive immediate attention. Other patients may be determined to be at reduced risk, and alerts may be sent to a physician for follow-up and/or referral to a mental health specialist, the next business day. Additionally, digitized information from a plurality of sources may be analyzed to monitor the progress of patients (e.g., during treatment and/or therapy) in an ongoing manner. For example, the system can assess changes in sentiment and determine whether a patient is improving, due to therapy and/or treatment.

This approach provides an improvement over current mental health management services and technologies, as it unifies communication between physicians, emergency personnel, patients, and mental health professionals, as well as aggregates and analyzes relevant patient information from multiple sources (e.g., biomarker testing, EMRs, and voice transcripts). This approach is integrated into a practical application, relying on NLP and machine learning techniques, biomarker and medical information analysis, and communication systems (e.g., email, text, cellular phones, or any other suitable communication channel, etc.) to analyze digitized data and provide notifications as needed.

Additionally, present techniques provide a system to health care providers, to automate and streamline access to mental health services to reduce the number of cases that go unreported or undiagnosed. Additionally, data provided from existing EMR and other electronic records may be analyzed to identify at-risk patients (e.g., with low risk) to provide early intervention, instead of delaying treatment until the condition of the patient deteriorates further. Additionally, the system can make predictions regarding patient progress, e.g., based on cohorts of individuals with similar profiles (e.g., based on EHR, biomarkers, etc.), or based on changes in determined sentiment (e.g., a patient whose sentiment becomes more positive would be expected to further improve with ongoing treatment).

It will be appreciated that the embodiments described above and illustrated in the drawings represent only a few of the many ways of implementing embodiments for automating detection and monitoring of mental health conditions.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing system employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, automated mental health condition detection and monitoring system 15, etc.). These systems may include any type of monitors and input devices (e.g., keyboard, mouse, voice recognition, etc.) to enter and/or view information.

It is to be understood that the software (e.g., automated mental health condition detection and monitoring system 15, including text generation engine 105, patient information aggregation engine 110, patient information extraction engine 115, mental health condition aspect mining engine 120, NLP sentiment analyzer engine 125, mental health condition monitoring engine 135, and flagging and alerts engine 140, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., automated mental health condition detection and monitoring system 15, including text generation engine 105, patient information aggregation engine 110, patient information extraction engine 115, mental health condition aspect mining engine 120, NLP sentiment analyzer engine 125, mental health condition monitoring engine 135, and flagging and alerts engine 140, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., automated mental health condition detection and monitoring system 15, including text generation engine 105, patient information aggregation engine 110, patient information extraction engine 115, mental health condition aspect mining engine 120, NLP sentiment analyzer engine 125, mental health condition monitoring engine 135, and flagging and alerts engine 140, etc.). The database system may be implemented by any number of any conventional or other databases, data stores or storage structures (e.g., files, databases, data structures, data or other repositories, etc.) to store information (e.g., mental condition training dataset 32, patient information dataset 34, biomarker dataset 36, patient risk dataset 38, etc.). The database system may be included within or coupled to the server and/or client systems. The database systems and/or storage structures may be remote from or local to the computer or other processing systems, and may store any desired data (e.g., mental condition training dataset 32, patient information dataset 34, biomarker dataset 36, patient risk dataset 38, etc.).

The present invention embodiments may employ any number of any type of user interface (e.g., Graphical User Interface (GUI), command-line, prompt, etc.) for obtaining or providing information (e.g., mental condition training dataset 32, patient information dataset 34, biomarker dataset 36, patient risk dataset 38, etc.), where the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, etc.). The interface screens may include any suitable actuators (e.g., links, tabs, etc.) to navigate between the screens in any fashion.

The output of the automated mental health condition detection and monitoring system 15 may include any information arranged in any fashion, and may be configurable based on rules or other criteria to provide desired information to a user (e.g., classification results, risk categories, sentiment scores, sentiment trajectories, etc.).

The present invention embodiments are not limited to the specific tasks or algorithms described above, but may be utilized for any application in which automated detection of text-based information is useful. For example, while the present examples are in the context of NLP, any suitable classifier may be used. Further, this approach may be generally applicable to mitigate any identifying or other information in any context, and is not limited to medical implementations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of detecting a mental health condition comprising:
   analyzing, via a processor, structured and unstructured information using natural language processing to extract information including clinical data values and medical concepts pertaining to a user, wherein the extracted information includes blood analysis for the user including biomarkers derived from genomic, proteomic, and/or immunoassay studies;
   evaluating, via the processor, reference medical information using natural language processing to correlate medical data with mental health conditions;
   determining, via the processor, a classification for a mental health condition of the user using a machine learning model and based on the extracted information and correlations, wherein determining the classification includes:
      performing sentiment analysis to determine values for sentiment of textual terms of the extracted information associated with the mental health conditions;
      assigning values to the biomarkers of the blood analysis associated with the textual terms for indicating at least one of the mental health conditions; and
      summing the values for sentiment of the textual terms with the values of the associated biomarkers to produce a score used for determining the classification;
   assigning, via the processor, the user to a segment of users based on the extracted information;
   indicating, via the processor, a treatment for the mental health condition of the user based on the classification and the assigned segment of users; and
   continually training the machine learning model, via the processor, based on new user data and verification of classifications as the new user data is analyzed and the classifications are verified.

2. The method of claim 1, wherein indicating the treatment further comprises:
   indicating, via the processor, one or more additional blood tests to perform based on the classification.

3. The method of claim 1, wherein the machine learning model includes a support vector machine.

4. The method of claim 1, wherein the unstructured information includes one or more from a group of: notes of a clinician, a patient journal, medical literature, and medical standards.

5. The method of claim 1, wherein the structured information includes one or more from a group of: blood work profiles, patient case files, electronic health records, and patient attributes.

6. The method of claim 1, wherein determining the classification for the mental health condition of the user further comprises:
   determining, via the processor, a risk of injury to the user due to the mental health condition of the user; and
   providing, via the processor, an alert of the mental health condition of the user in response to the risk satisfying a threshold.

7. The method of claim 1, wherein the classification is based on medical mental disorder standards.

8. An apparatus for detecting a mental health condition, the apparatus comprising:
   one or more processors;
   one or more computer readable storage media;
   program instructions stored on the one or more computer readable storage media for execution by at least one of the one or more processors, the program instructions comprising instructions to:
      analyze structured and unstructured information using natural language processing to extract information including clinical data values and medical concepts pertaining to a user, wherein the extracted information includes blood analysis for the user including biomarkers derived from genomic, proteomic, and/or immunoassay studies;
      evaluate reference medical information using natural language processing to correlate medical data with mental health conditions;
      determine a classification for a mental health condition of the user using a machine learning model and based on the extracted information and correlations, wherein determining the classification includes:
         performing sentiment analysis to determine values for sentiment of textual terms of the extracted information associated with the mental health conditions;
         assigning values to the biomarkers of the blood analysis associated with the textual terms for indicating at least one of the mental health conditions; and
         summing the values for sentiment of the textual terms with the values of the associated biomarkers to produce a score used for determining the classification;
      assign the user to a segment of users based on the extracted information;
      indicate a treatment for the mental health condition of the user based on the classification and the assigned segment of users; and
      continually train the machine learning model based on new user data and verification of classifications as the new user data is analyzed and the classifications are verified.

9. The apparatus of claim 8, wherein the program instructions further comprise instructions to:
   indicate one or more additional blood tests to perform based on the classification.

10. The apparatus of claim 8, wherein indicating the treatment further comprises:
    indicating a score card including one or more mental health conditions that the user is at-risk of developing, a listing of users subdivided according to risk level, treatment plans, and outcomes.

11. The apparatus of claim 8, wherein the unstructured information includes one or more from a group of: notes of a clinician, a patient journal, medical literature, and medical standards.

12. The apparatus of claim 8, wherein the structured information includes one or more from a group of: blood work profiles, patient case files, electronic health records, and patient attributes.

13. The apparatus of claim 8, wherein the program instructions further comprise instructions to:
    determine a risk of injury to the user due to the mental health condition of the user; and
    provide an alert of the mental health condition of the user in response to the risk satisfying a threshold.

14. The apparatus of claim 8, wherein the classification is based on medical mental disorder standards.

15. A computer program product for detecting a mental health condition, the computer program product comprising one or more computer readable storage media collectively having program instructions embodied therewith, the program instructions executable by a computer to cause the computer to:

analyze structured and unstructured information using natural language processing to extract information including clinical data values and medical concepts pertaining to a user, wherein the extracted information includes blood analysis for the user including biomarkers derived from genomic, proteomic, and/or immunoassay studies;

evaluate reference medical information using natural language processing to correlate medical data with mental health conditions;

determine a classification for a mental health condition of the user using a machine learning model and based on the extracted information and correlations, wherein determining the classification includes:

performing sentiment analysis to determine values for sentiment of textual terms of the extracted information associated with the mental health conditions;

assigning values to the biomarkers of the blood analysis associated with the textual terms for indicating at least one of the mental health conditions; and summing the values for sentiment of the textual terms with the values of the associated biomarkers to produce a score used for determining the classification;

assign the user to a segment of users based on the extracted information;

indicate a treatment for the mental health condition of the user based on the classification and the assigned segment of users; and continually train the machine learning model based on new user data and verification of classifications as the new user data is analyzed and the classifications are verified.

16. The computer program product of claim 15, wherein the program instructions further cause the computer to indicate one or more additional blood tests to perform based on the classification.

17. The computer program product of claim 15, wherein the machine learning model includes a support vector machine.

18. The computer program product of claim 15, wherein the unstructured information includes one or more from a group of: notes of a clinician, a patient journal, medical literature, and medical standards.

19. The computer program product of claim 15, wherein the structured information includes one or more from a group of: blood work profiles, patient case files, electronic health records, and patient attributes.

20. The computer program product of claim 15, wherein the program instructions further cause the computer to:

determine a risk of injury to the user due to the mental health condition of the user; and provide an alert of the mental health condition of the user in response to the risk satisfying a threshold.

* * * * *